United States Patent [19]

Someya

[11] Patent Number: 4,540,584

[45] Date of Patent: Sep. 10, 1985

[54] COMPOSITION FOR PROMOTION OF HEALTH

[76] Inventor: Nobuo Someya, No. 16-6, Kami-Ikebukuro 3-chome, Toshima-Ku, Tokyo, Japan

[21] Appl. No.: 566,456

[22] Filed: Dec. 28, 1983

[30] Foreign Application Priority Data

Dec. 28, 1982 [JP] Japan .............................. 57-233889

[51] Int. Cl.³ .................... A61K 33/08; A61K 33/04; A61K 33/22; A61K 33/32
[52] U.S. Cl. .................................... 424/156; 424/140; 424/144; 424/145; 424/148; 424/149; 424/157; 424/163; 424/147; 426/74
[58] Field of Search ............... 424/357, 148, 157, 144, 424/147, 140, 145, 149, 163; 426/74

[56] References Cited

U.S. PATENT DOCUMENTS

| | | | |
|---|---|---|---|
| 50,578 | 10/1865 | Hamilton | 424/49 |
| 801,317 | 10/1905 | James | 424/49 |
| 826,990 | 7/1906 | Cartwright | 426/74 |
| 1,645,703 | 10/1927 | Lapp | 426/74 |
| 2,059,396 | 11/1936 | Ripert | 424/49 |
| 2,152,438 | 3/1939 | McHan | 426/74 |
| 2,512,537 | 7/1950 | Zellers | 426/74 |
| 2,820,000 | 1/1958 | Menzies | 424/49 |
| 2,868,644 | 1/1959 | Eisenberg | 426/74 |
| 2,999,752 | 9/1961 | Webb | 426/74 |
| 3,944,661 | 3/1976 | Colodney et al. | 424/49 |
| 4,102,992 | 7/1978 | Davis | 424/49 |

OTHER PUBLICATIONS

Chem. Abstracts, vols. 99, (1983) to 1, (1906), entry "Corals".

*Primary Examiner*—Shep K. Rose
*Attorney, Agent, or Firm*—Sughrue, Mion, Zinn, Macpeak & Seas

[57] ABSTRACT

Coral sand obtained from living skeletons or semi-fossils of hermatypic coral or reef-building coral is ground into about 150 to 500 mesh and the resulting coral sand powders are provided as drinkables or tablets for promotion of health.

20 Claims, No Drawings

COMPOSITION FOR PROMOTION OF HEALTH

BACKGROUND OF THE INVENTION

1. Field of the Invention

The present invention relates to a composition for promotion of health and more particularly, to a composition for promotion of health comprising coral sand as an effective component.

2. Development of the Invention

Tap water is weakly acidic property due to the presence of residual chlorine therein. In recent years the consumption of so-called acidic foodstuffs such as meat or the like has increased because of improved diet but such is attended by a harmful influence. On the other hand, it is concerned that decayed teeth and constitutional tendencies to fracture of a bone have increased due to calcium poverty or the like, particularly in babies and children, irrespective of remarkable improvement in their physiques.

In view of the foregoing circumstances, the present invention has been accomplished.

SUMMARY OF THE INVENTION

The present invention is based on the discovery that coral sand obtained by grinding living skeletons and semi-fossils of hermatypic coral or reef-building coral (hereafter referred to as "reef-building coral") contains calcium carbonate as a main component and a variety of minerals required by the human body in ecologically chemical proportions. That is, the present invention is directed to a composition for promotion of health comprising coral sand as an effective component.

DESCRIPTION OF THE PREFERRED EMBODIMENTS

The composition of the present invention is characterized in that coral sand is contained as an effective component.

Coral sand which is obtained from living skeletons and semi-fossils of reef-building coral, contains calcium carbonate ($CaCO_3$) as a main component (about 95%); magnesium, strontium, sodium, potassium, phosphorus and chlorine, which are important bio-elements; and further trace quantities of essential inorganic vitamin elements such as iron, copper, zinc, manganese, cobalt, chromium, boron, etc., as shown in Table 1 below.

TABLE 1

| Analyte | A | C | G | AA | BB |
|---|---|---|---|---|---|
| Boron (B) | ≦0.01 | ≦0.01 | ≦0.01 | ≦0.01 | ≦0.01 |
| Sodium (Na) | 0.26 | 0.25 | 0.33 | 0.29 | 0.32 |
| Magnesium (MgO) | 1.92 | 1.52 | 1.89 | 1.68 | 2.43 |
| Aluminum ($Al_2O_3$) | | 0.088 | 0.026 | 0.030 | 0.028 |
| Silicon ($SiO_2$) | 0.067 | 0.32 | 0.044 | 0.078 | 0.071 |
| Phosphorus ($PO_4$) | 0.071 | 0.069 | 0.061 | 0.057 | 0.062 |
| Sulfur (S) | 0.19 | 0.17 | 0.17 | 0.20 | 0.19 |
| Chlorine (Cl) | 0.013 | 0.012 | 0.024 | 0.023 | 0.008 |
| Potassium (K) | 0.0084 | 0.0076 | 0.0094 | 0.0080 | 0.0092 |
| Calcium (CaO) | 53.33 | 53.48 | 53.14 | 53.16 | 53.09 |
| Titanium ($TiO_2$) | 0.0015 | 0.00096 | 0.00034 | 0.00041 | 0.00043 |
| Chromium (Cr) | 0.0022 | 0.0022 | 0.0021 | 0.0022 | 0.0020 |
| Manganese (Mn) | 0.0019 | 0.0019 | 0.00080 | 0.0011 | 0.00092 |
| Iron (Fe) | | 0.0087 | 0.0052 | | 0.0073 |
| Cobalt (Co) | 0.0012 | 0.0011 | 0.0016 | 0.0011 | 0.0012 |
| Nickel (Ni) | 0.0011 | 0.0013 | 0.0014 | 0.0013 | 0.0011 |
| Copper (Cu) | 0.00056 | 0.00056 | 0.00056 | 0.00050 | 0.00056 |
| Zinc (Zn) | 0.00034 | 0.00050 | 0.00046 | 0.00062 | 0.00046 |
| Strontium (Sr) | 0.32 | 0.38 | 0.44 | 0.45 | 0.85 |
| Molybdenum (Mo) | ≦0.00005 | ≦0.00005 | ≦0.00005 | ≦0.00005 | ≦0.00005 |
| Carbonic acid ($CO_2$) | 40.8 | 40.9 | 40.5 | 40.7 | 40.5 |
| Ignition Loss (450° C./2h) | 2.85 | 2.57 | 3.05 | 3.01 | 2.56 |

The above results were obtained with various coral sand samples A, C and G (obtained from the Ishigakijima Island), AA and BB (obtained from the Okinawa Main Island) by Osaka Chemical Analysis Center Co., Ltd., upon request.

These elements shown in Table 1 above which are contained in typical Examples of naturally occurring coral sand are accumulated and calcified through life activity of reef-building coral that is coelenterates. Accordingly, coral sand has an ecologically chemical proportion, unlike food additives such as calcium carbonate and the like obtained purely by chemical treatment. Due to such ecological consideration, the composition of the presennt invention is safe for the human body and becomes a source of replenishing minerals of good quality, especially a source of replenishing calcium.

Turning to the process for producing the composition for promotion of health in accordance with the present invention, the process involves firstly washing naturally occurring coral sand with water to desalinated it, then disinfecting and drying the desalinated coral sand at temperatures of about 80° to about 150° C., preferablly 90° to 120° C., and, grinding the disinfected and dried coral sand into about 150 to about 500 mesh, preferably 200 to 450 mesh. The grinding can also be effected either by freeze drying the disinfected and dried coral sand at temperatures of about $-180°$ C. to $-200°$ C. in a nitrogen atmosphere, or in a state where coral sand has been kneaded together with seawater or fountain water.

The reef-building coral employed as a raw material for preparing coral sand is known to be the leading part in building coral reef because of skeletogenesis or calcification promoted by the action of Zooxanthella or endozoic algae present in its body. The optimum water temperature for growth of the reef-building coral is between about 25° and about 29° C. The reef-building coral is geometrically located generally in the tropical and sub-tropical zones. Representative examples of reef-building coral include coral belonging to the order Madreporaria, Helioporida of the order Coenothecalia, Tubipora of the order Stolonifera, Millepora of the order Milleporina, etc.

The thus obtained finely divided coral sand powders are extremely finely porous and have high solubility in water. The so obtained coral sand powders may be dissolved in water (the powders dissolve in the form of ions) as they are and the resulting solution can be provided as drinking water. Alternatively, the fine powders of the coral sand may be formulated as granules, tablets, emulsions, pills, suspension concentrates, etc., in the presence or absence of binders. Granules are usually manufactured by agglomeration or impregnation techniques. Generally granules will contain 0.5 to 25% by weight of the coral sand fine powders and 0 to 10% by weight of additives, if necessary and desired, such as stabilizers, slow release modifiers and binders. Tablets or pills may be manufactured in conventional manners, by mixing with binders such as starch, gelatin, etc. and the tabletting the mixture using a tabletting machine.

The composition of the present invention may also contain other ingredients, for example, various nutrients such as vitamins (vitamins A, B, C, E, F, etc.), sugars (glucose, fructose, sucrose, maltose, or the like), etc. Further, the coral sand powders per se may also be employed as additives to various foodstuffs.

The composition for promotion of health in accordance with the present invention is useful for replenishing especially calcium. In addition, the composition of the present invention can also replenish magnesium, strontium, potassium, phosphorus, copper, etc., which are bio-elements, and further trace quantities of essential inorganic vitamin elements such as iron, manganese, potassium, etc. By drinking it after dissolving the coral sand powders in tap water, etc., a delicious mineral water showing weakly alkaline property which is free from the so-called bleaching powder smell can be obtained. This is assumed to be because an acid ($H_3O^+$) released during the course of chlorination of tap water would be neutralized by the action of the coral sand which comprises carbonate as a main component, whereby the system would be rendered weakly alkaline in the presence of calcium ions ($Ca^{2+}$), as shown below:

$$Cl_2 + H_2O \geqq HCl + HClO \quad (1)$$

$$HCl + H_2O \geqq H_3O^+ + Cl^- \quad (2)$$

$$HClO + H_2O \geqq H_3O^+ + Cl^- + O\uparrow \quad (3)$$

$$2CaCO_3 + 2H_2O^+ \geqq 2Ca^{2+} + 2HCO_3 + 2H_2O \quad (b\ 4)$$

$$Cl_2 + H_2O + 2CaCO_3 \rightarrow 2Ca^{2+} + 2HCO_3^- + 2Cl^- + O\uparrow \quad (5)$$

The composition for promotion of health in accordance with the present invention is more effective when given to adults generally at a daily dose of 1.0 to 10 g.

As explained above, the composition for promotion of health in accordance with the present invention comprises as an effective component the coral sand containing calcium carbonate as a main component and further containing various inorganic materials necessary for the human body in an ecologically chemical proportion. Therefore, the composition for promotion of health of the present invention can improve diet which is inclined to take acidic foodstuffs. In particular, calcium which tends to be lacking in babies and children can be spontaneously replenished and at the same time, the so-called inorganic vitamin elements can be provided by taking the composition for promotion of health of the present invention; thus contributing to promotion of health.

The present invention will be described in more detail with reference to the examples below. Percentages are weight, temperature is room temperature and pressure is atmospheric pressure, unless otherwise indicated.

EXAMPLE 1

Coral sand A shown in Table 1, obtained from the Ishigakijima Island, was washed with water to effect desalination. After the absence of chlorine had been confirmed by the Mohr test, the coral sand was then disinfected and dried by heating at about 100° C. The thus disinfected and dried coral sand was then ground at room temperature to pass a sieve of 350 mesh.

The resulting coral sand powders were dissolved in water to give a composition containing 20% of the coral sand. The composition showed a pH of about 7.1.

EXAMPLE 2

Coral sand C shown in Table 1, obtained from the Ishigakijima Island, was treated in a manner similar to Example 1 except that the grinding was performed by freeze drying the dried coral sand at $-180°$ to $-200°$ C. in a nitrogen flow. The resulting coral sand powders had a size of about 200 to about 300 mesh. An aqueous solution of the coral sand powders showed a pH of about 7.2.

While the invention has been described in detail and with reference to specific embodiments thereof, it will be apparent to one skilled in the art that various changes and modifications can be made therein without departing from the spirit and scope thereof.

What is claimed is:

1. A mineral supplement, comprising:
    coral sand as an effective component in an amount sufficient to provide calcium carbonate and other minerals as a mineral supplement for humans;
    wherein said coral sand is in the form of a fine powder of a particle size passing about 150 to 500 mesh.

2. The mineral supplement according to claim 1, wherein said coral sand is in the form of a fine powder of particle size passing about 200 to 450 mesh.

3. The mineral suupplement according to claim 1 wherein said coral sand is obtained by desalting naturally occurring coral sand, disinfecting and drying the desalted coral sand by heating at about 80° to about 150° C. and then grinding the disinfected and dried coral sand into about 150 to about 500 mesh.

4. The mineral supplement according to claim 3 wherein said griding is performed at room temperature.

5. The mineral supplement according to claim 4 wherein said grinding is performed by freeze drying the disinfected and dried coral sand at about $-180°$ to $-200°$ C. in a nitrogen atmosphere.

6. The mineral supplement according to claim 1 wherein said coral sand of about 150 to about 500 mesh is formulated in tablets in the presence of a binder.

7. The mineral supplement according to claim 6 wherein said binder is selected from starch and gelatin.

8. The mineral supplement according to claim 1 wherein said coral sand is obtained from the Ishigakijima Island.

9. The mineral supplement according to claim 1 wherein said coral sand is obtained the Okinawa Main Island.

10. A mineral supplement comprising coral sand as an effective component produced by the process of obtaining naturally occurring coral sand, desalting said coral sand, disinfecting and drying the desalted coral sand by heating it at about 80° to about 150° C. and then grinding the disinfected and dried coral sand into a fine powder of a particle size passing about 150 to about 500 mesh.

11. A process of administering a mineral supplement to a human comprising administering to said human coral sand as an effective component in an amount sufficient to provide calcium carbonate and other minerals as a mineral supplement for humans wherein said coral sand is in the form of a fine powder of a particle size passing about 150 to about 500 mesh.

12. The process of claim 11, wherein a binder selected from the group consisting of starch and gelatin is present in a mineral supplement formulation containing said coral sand.

13. A mineral supplement is claimed in claim 3, wherein heating is carried out at 90°–120° C.

14. The mineral supplement of claim 1, wherein said fine powders of coral sand are formulated as granules, tablets, emulsions, pills or suspension concentrates.

15. The process of claim 11, wherein said mineral supplement is formulated as granules, tablets, emulsions, pills or suspension concentrates.

16. The mineral supplement of claim 14, wherein said granules contain 0.5 to 25% by weight of the coral sand fine powders.

17. The mineral supplement of claim 16, wherein said granules contain 0-10% by weight of additives selected from the group of stabilizers, slow release modifiers and binders.

18. The process of claim 11, wherein said mineral supplement is given to adults at a daily dose of 1.0 to 10 g.

19. The mineral supplement of claim 1, wherein said mineral supplement is used to provide calcium carbonate and other minerals to humans.

20. The mineral supplement of claim 1 wherein the coral sand is obtained from Ishiyakijima Islands or Okinawa Main Island, said coral sand containing B, Na, MgO, $Al_2O_3$, $SiO_2$, $PO_4$, S, Cl, K, CaO, $TiO_2$, Cr, Mn, Fe, Co, Ni, Cu, Zn, Sr and Mo.

* * * * *